US006060518A

United States Patent [19]
Kabanov et al.

[11] Patent Number: 6,060,518
[45] Date of Patent: May 9, 2000

[54] POLYMER COMPOSITIONS FOR CHEMOTHERAPY AND METHODS OF TREATMENT USING THE SAME

[75] Inventors: Alexander V. Kabanov, Omaha, Nebr.; Valery Yu. Alakhov, Quebec, Canada

[73] Assignee: Supratek Pharma Inc., Montreal, Canada

[21] Appl. No.: 08/698,570

[22] Filed: Aug. 16, 1996

[51] Int. Cl.[7] .............................. A61K 9/08; A61K 47/34
[52] U.S. Cl. ...................... 514/781; 514/777; 514/772.2; 514/788
[58] Field of Search .......................... 424/78.08; 541/781

[56] References Cited

U.S. PATENT DOCUMENTS 4,769,250  9/1988  Forssen ................................... 424/450

OTHER PUBLICATIONS

Valery Yu. Alakhov, et al., Hypersensitization of Multidrug Resistant Human Ovarian Carcinoma Cells by Pluronic P85 Block Copolymer, *Bioconjugate Chemical*, 1996, pp. 209–216.

Irina Astafieva et al., "Enhancement of the polycation–mediated DNA uptake and cell transfection with Pluronic P85 block copolymer", *FEBS Letters*, 389, (1996), 278–280.

Sandrine Cammas and Kazunori Kataoka, "Functional poly [(ethylene oxide)–co–(β–benzyl–L–aspartate)] polymeric micelles: block copolymer synthesis and micelles formation", *Macromol. Chem. Phys.*, 196, 1899–1905 (1995).

S. Cammas, et al., "Poly(ethylene oxide–co–β–benzyl L–aspartate) Block Copolymers: Influence of the Poly(ethylene oxide) Block on the Conformation of the Poly (β–benzyl L–aspartate) Segment in Organic Solvents", *Macromolecules*, vol. 29, No. 9, pp. 3227–3231, 1996.

Stanley S. Davis, et al., "Polymers in drug delivery", *Biological Aspects*, 1984, pp. 660–666.

Michael Draper, et al., "Solubilisation of Drugs in Micellar Systems Studied by Eluent Gel Permeation Chromatography", *Solubilisation of Drugs*, 1995, pp. 1231–1237.

S.A. Hagan, et al., "Polylactide–Poly(ethylene glycol) Copolymers as Drug Delivery Systems. 1. Characterization of Water Dispersible Micelle–Forming Systems", *Langmuir*, vol. 12, No. 9, 1996, pp. 2153–2161.

Alexander V. Kabanov et al., "A new class of drug carriers: micelles of poly(oxyethylene)–poly(oxypropylene) block copolymers as microcontainers for drug targeting from blood in brain", *Journal of Controlled Release*, 22 (1992), pp. 141–158.

Joseph C. Salamone, Editor–in–Chief, "Block Copolymers Micelles", *Polymeric Materials Encyclopedia*, vol. 1, A–B, 1996, pp. 757–760.

Alexander V. Kabanov, et al., "Micelle Formation and Solubilization of Fluorescent Probes in Poly(oxyethylene–b–oxypropylene–b–oxethylene) Solutions", *Macromolecules*, 1995, 28, 2303–2314.

Alexander V. Kabanov et al., "Pluronic Micelles as a Tool For Low–Molecular Compound Vector Delivery into a cell: Effect of *Staphylococcus aureus* enterotoxin B on Cell Loading With Micelle Incorporated Fluorescent Dye", *Biochemistry International*, vol. 26, No. 6, May 1992, pp. 1035–1042.

A.V. Kabanov, et al., "The neuroleptic activity of haloperido increases after its solubilization in surfactant miscelles", *FEB*, vol. 258, No. 2, Dec. 1989, pp. 343–345.

Alexander V. Kabanov, et al., *Bioconjugate Chemistry*, vol. 6, No. 6, Nov./Dec. 1995, pp. 639–714.

Russell A. Gaudiana, Editor, J.M.S.—Pure Appl. Chem., A31(11), pp. 1759–1769, (1994).

N. Ogata, et al., "Advanced Biomaterials in Biomedical Engineering and Drug Delivery Systems", 1996, pp. 95–100.

Glen S. Kwon, et al., "Block copolymer micelles as long–circulating drug vehicles", *Advanced Drug Delivery Reviews*, 16, (1995), pp. 295–309.

G. Kwon, et al., Micelles Based on AB Block of Copolymers of Poly(ethylene oxide) and Poly(β–benzyl L–aspartate), Langmuir, 1993, 9, pp. 945–949.

Glen S. Kwon, et al., "Physical Entrapment of Adriamycin in AB Block Copolymer Micelles", Pharmaceutical Research, vol. 12, No. 2, 1995, 192–195.

G. Kwon, et al., Micelles Based on AB Block of Copolymers of Poly(ethylene oxide) and Poly(β–benzyl L–aspartate), *Langmuir*, 1993, 9, pp. 945–949.

Sung Bum La, et al., "Preparation and Characterization of the Micelle–Forming Polymeric Drug Indomethacin–Incorporated Poly(ethyleneoxide)–Poly(β–benzyl L–aspartate) Block Copolymer Micelles", *Journal of Pharmaceutical Sciences*, vol. 85, No. 1, Jan. 1986, 85–90.

Shan–Yang Lin, et al., "Kinetic Studies on the Stability of Indomethacin in Alkaline Aqueous Solution Containing Poly(oxyethylene) poly(oxypropylene) Surface–active Block Copolymers" 1985.

Shang–Yang Lin, et al., "Pluronic Surfactants Affecting Diazepam Solubility, Compatibility, and Adsorption from i.v. Admixture Solutions", *Journal of Parenteral Science & Technology*, vol. 41, No. 3, May/Jun. 1987, pp. 83–87.

Shan–Yang Lin, et al., "The Influence of Three Poly(oxyethylene)poly(oxypropylene) Surface–active Block Copolymers on The Solubility Behavior of Indomethacin", *Pharm. Acta Helv.*, vol. 60, No. 12, 1985, pp. 339–344.

P.J. Morgan, et al., "Interactions of a model block copolymer drug delivery system with two serum proteins and myoglobin", *Biochemical Society Transactions*, vol. 18, pp. 1021–1022, 1990.

(List continued on next page.)

*Primary Examiner*—Peter F. Kulkosky
*Attorney, Agent, or Firm*—Mathews, Collins, Shepherd & Gould, P.A.

[57] ABSTRACT

Improved antineoplastic compositions comprising an antineoplastic agent combined with a pluronic and a water-soluble non-toxic homopolymer resulting in a decrease of toxicity and/or an increase in anti-cancer activity, and methods of treatment using such formulations.

10 Claims, No Drawings

OTHER PUBLICATIONS

R. Paradis, et al., "Use of Pluronic Micelles to Overcome Multidrug Resistance", *International Journal of Oncology*, 1994, pp. 1305–1308.

Piskin, et al., *Journal of Biomaterials Science, Polymer Edition*, 1995, pp. 359–373.

A. Rolland, et al., "New Macromolecular Carriers for Drugs. I. Preparation and Characterization of Poly(oxyethlene–b–isoprene–b–oxyethylene) Block Copolymer Aggregates", New Macromolecular For Drugs. I., 1991, pp. 1195–1203.

Vladimir I. Slepnev, et al., Micelles of Poly(oxyethylene-)–Poly(oxypropylene) Block Copolymer (Pluronic) As A Tool For Low–Molecular Compound Delivery Into A Cell: Phosphorylation Of Intracellular Proteins With Micelle Incorporated [r–32p]ATP 1, *Biochemistry International*, vol. 26, No. 4, Mar. 1992, pp. 587–595.

V.S. Trubetskoy, et al., "Amphiphilic radioplaque iodine–containing block–copolymer as micellar polymeric carrier with controlled in vivo performance", Proceed. Intern. Symp. Control. Rel. Bioact. Mater., 21, 1994, pp. 676–677.

Annie Venne, et al., "Hypersensitizing Effect of Pluronic L61 on Cytotoxic Activity, Transport, and Subcellular Distribution of Doxorubicin in Multiple Drug–resistant Cells", *Cancer Research* 56, pp. 3626–3629, Aug. 15, 1996.

Masayuki Yokoyama, et al., Characterization and Anticancer Activity of the Micelle–forming Polymeric Anticancer Drug Adriamycin–conjugated Poly(ethylene glycol)–Poly(aspartic acid) Block Copolymer, Cancer Research, 50, Mar. 15, 1990, pp. 1693–1700.

Masayuki Yokoyama, et al., "Polymer Micelles As Novel Drug Carrier: Adriamycinm–Conjugated Poly(Ethylene Glycol)–Poly(Aspartic Acid) Block Copolymer", *Journal of Controlled Release*, 11, (1990), pp. 269–278.

Masayuki Yokoyama, et al., "Preparation of adriamycin-–conjugated poly(ethylene glycol)–poly(aspartic acid) block copolymer", *Makromol. Chem.*, 8, (1987), pp. 431–435.

Masayuki Yokoyama, et al., "Preparation of Micelle–Forming Polymer–Drug Conjugates", American Chemical Society, 1992, pp. 295–301.

Masayuki Yokoyama, et al., Stabilization of Disulfide Linkage in Drug–Polymer–Immunoglobulin Conjugate By Microenvironmental Control, *Biochemical and Biophysical Research Communications*, vol. 164, No. 3, 1989, 1234–1239.

Masayuki Yokoyama, et al., "Toxicity and Antitumor Activity against Solid Tumors of Micelle–forming Polymeric Anticancer Drug and Its Extremely Long Circulation in Blood", *Cancer Research*, 51, 1991.

Xichen Zhang, et al., "Development of amphiphilic diblock copolymers as micellar carriers of taxol", *International Journal of Pharmaceutics*, 132, (1996), pp. 195–206.

POLYMER COMPOSITIONS FOR CHEMOTHERAPY AND METHODS OF TREATMENT USING THE SAME

The present invention relates to improvements in antineoplastic formulations and methods of treatment using such improved formulations.

BACKGROUND OF THE INVENTION

A variety of antineoplastic agents are presently in use in chemotherapy. See generally Cuttings Handbook of Pharmacology, 7th Ed., Chapter 13, Scaky and Barnes. However, because of their often complex structure, antineoplastic agents are known to exhibit low stability in the bloodstream. Often, chemotherapeutic agents are extremely insoluble, and are thus poorly transported across cell membranes. Additionally, the effective amount of antineoplastic agents can be greatly reduced through binding of such agents with plasmoproteins, as well as other non-specific interactions in the bloodstream occurring prior to the agents reaching the target. Multidrug resistance (MDR) is a further complication observed with such chemotherapeutic agents, resulting in host resistance to structurally different antineoplastic agents.

Certain antineoplastic agents currently in use have demonstrated toxicity in patients. It is thus desirable to either {i} decrease toxicity of these compositions, {ii} increase their overall anti-cancer activity, or {iii} both. It is similarly desirable to overcome MDR in patients receiving chemotherapeutic agents.

DETAILED DESCRIPTION OF THE INVENTION

The above difficulties can be overcome by administration of antineoplastic agents incorporated into a composition comprising an amphiphilic block copolymer and a non-toxic water-soluble homopolymer or random copolymer.

The invention thus relates to improved compositions comprising an antineoplastic agent combined with an amphiphilic block copolymer and a water-soluble non-toxic homopolymer or random polymer. It has been found that this combination results in {i} a decrease of toxicity, {ii} an increase in anti-cancer activity, or {iii} both. The combinations are further capable of reducing or avoiding MDR in patients suffering from neoplasm.

The advantageous properties of the resultant compositions are achieved through the combination of at least one antineoplastic agent, a water-soluble or random non-toxic polymer, and a hydrophobic copolymer, i.e., where the copolymers contain poly(oxypropylene), or POP, content greater than 50 percent.

In one embodiment, the recited homopolymers are water soluble. These polymers can be ionic or capable of being tonically charged in a pH-dependent manner. The preferred molecular mass range for the nontoxic water-soluble homopolymer or random copolymer is from about $0.5 \times 10^3$ to $0.5 \times 10^5$. The preferred concentration of these polymers in mixture is from about $1 \times 10^{-4}$ to about 25% w/v.

Where a homopolymer is used, the homopolymer is preferably poly(ethylene oxide), or PEO. Where block copolymers are used, the block copolymers are preferably poly(oxyethylene)-poly(oxypropylene) block copolymers. In these POE-POP block copolymers, it has been found that hydrophobe (POP) concentrations greater than 50% are advantageous.

The block copolymers of poly(oxyethylene)-poly(oxypropylene) generally are characterized by one of the following structural formulae:

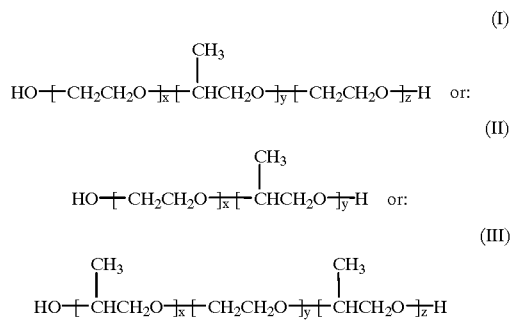

in which each of x and z, independently of one another, has a value of from about 5 to about 100, and y has a value of from about 20 to about 80. Such block copolymers are known. See Schmolka, *Loc. Cit.*, 82(7), 25–30 (1967); Stanton, *Am. Perfumer. Cosmet.*, 72(4), 54–58 (1958); and *Nonionic Surfactants*, Schick, Ed., 300–371 (Dekker, N.Y., 1967). A number of these copolymers are commercially available under the generic names of "pluronics" and "poloxamers".

The hydrophobic/hydrophilic properties of a given block copolymer are dependent upon the ratio of oxypropylene groups to the number of oxyethylene groups. Selecting the ratio of oxypropylene groups to oxyethylene groups involves the use of mixtures of different block copolymers of POE-POP to achieve an optimal balance for a given anti-neoplastic agent, or mixture of anti-neoplastic agents, preserving the optimal particle size.

A variety of copolymers are suitable for use in the present invention. The present compositions can utilize, but are not limited to, the following copolymers:

| Pluronic | Hydrophobe Weight | Hydrophobe Percentage |
| --- | --- | --- |
| L31 | 950 | 90% |
| F35 | 950 | 50% |
| L42 | 1200 | 80% |
| L43 | 1200 | 70% |
| L44 | 1200 | 60% |
| L61 | 1750 | 90% |
| L62 | 1750 | 80% |
| L63 | 1750 | 70% |
| L64 | 1750 | 60% |
| P65 | 1750 | 50% |
| F68 | 1750 | 20% |
| L72 | 2050 | 80% |
| P75 | 2050 | 50% |
| L81 | 2250 | 90% |
| P84 | 2250 | 60% |
| P85 | 2250 | 50% |
| F87 | 2250 | 30% |
| F88 | 2250 | 20% |
| L92 | 2750 | 80% |
| F98 | 2750 | 20% |
| L101 | 3250 | 90% |
| P103 | 3250 | 70% |
| P104 | 3250 | 60% |
| P105 | 3250 | 50% |
| F108 | 3250 | 20% |
| L121 | 4000 | 90% |
| L122 | 4000 | 80% |
| L123 | 4000 | 70% |

-continued

| Pluronic | Hydrophobe Weight | Hydrophobe Percentage |
|---|---|---|
| F127 | 4000 | 30% |
| 10R5 | 1000 | 50% |
| 10R8 | 1000 | 20% |
| 12R3 | 1200 | 70% |
| 17R2 | 1700 | 80% |
| 17R1 | 1700 | 90% |
| 17R2 | 1700 | 80% |
| 17R4 | 1700 | 60% |
| 17R8 | 1700 | 20% |
| 22R4 | 2200 | 60% |
| 25R1 | 2500 | 90% |
| 25R2 | 2500 | 80% |
| 25R4 | 2500 | 60% |
| 25R5 | 2500 | 50% |
| 25R8 | 2500 | 50% |
| 31R1 | 3100 | 90% |
| 31R2 | 3100 | 80% |
| 31R4 | 3100 | 60% |

It has been found that the effectiveness of the block copolymers of the instant invention in enhancing the potency of chemotherapeutic drugs, decreasing toxicity, and/or in reducing or reversing MDR depend upon the hydrophobe percentage and the hydrophobe weight. Overall effectiveness of the compositions has been found to increase with an increase in either hydrophobe weight, hydrophobe percentage, or both. It has been found for example that L61 is more effective than P85 which in turn is more effective than F108, which in turn is more effective than F68. One skilled in the art, however, can readily determine the most preferable copolymer based upon the specific circumstances of its intended use.

In accordance with the present invention, the preferred homopolymer is poly(ethylene oxide), or PEO, represented by the formula:

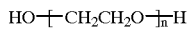

wherein n is such that the molecular mass range of PEO is from about $0.5 \times 10^3$ to about $0.5 \times 10^5$. More preferred is from about $1 \times 10^3$ to about $0.2 \times 10^5$, and most preferred is from about $1.5 \times 10^3$ to about $0.15 \times 10^5$.

The present application is not, however, limited to the use of PEO. Other water-soluble polymers will work in accordance with the present invention. Suitable water-soluble polymers include without limitation: N-(2-hydroxypropyl)-methacrylamide copolymers, poly(ortho esters), poly(vinyl pyrrolidone), poly(vinyl alcohol), polysaccharides and their derivatives, including dextrane and heparin.

In a most preferred embodiment, the composition comprises doxorubicin as the antineoplastic agent, Pluronic L61 as the block copolymer, and PEO. Other anthracycline antibiotics such as daunorubicin and epirubicin are similarly most preferred. Pluronic L61 is characterized by hydrophobe (POP) content of at least about 90%. It will be appreciated, however, that the present invention is not limited to the recited hydrophobic pluronic polymers.

A variety of antineoplastic agents are suitable for use in accordance with the present invention. These include, but are not limited to, alkaloids such as vinblastine, colchicine, and demecoline; anthracycline antibiotics, including those of the rhodomycin group (e.g., daunorubicin, doxorubicin or epirubicin), those of the mitomycin group (e.g., mitomycin C and N-methylmitomycin C), those of the bleomycin group (e.g., bleomycin $A_2$), and antifolates (including methotrexate, aminopteran, and dideazatetrahydrofolic acid). Mixtures of several of these agents is contemplated within the scope of the invention.

It will be appreciated that the invention is not directed to the underlying anti-neoplastic activity of these agents, but rather to an improvement in the manifestation of this activity through formulation. The present compositions can be administered parenterally in aqueous formulations, alone or in combination with other therapeutic agents, including other antineoplastic agents, steroids, etc., to a mammal suffering from neoplasm and in need of treatment. Such parenteral routes of administration include intramuscular, intrathecal, intraperitoneal, intravenous, and intra-arterial. Isotonic micellular solutions of one or more block copolymers incorporating one or more antineoplastic agents can be used for parenteral administration. Dosages typically are those associated with the specific antineoplastic agent, although the regimen must be titrated to the particular neoplasm, the condition of the patient, and the specific response. Thus, the specific dosage will be determined by the attending physician or caretaker, based upon the individual circumstances of the patient. For example, an isotonic micellular solution of daunorubicin is administered to provide about 1 mg of daunorubicin per kg of body weight. In contrast, vinblastine is administered in a similar fashion, but in accordance with conventional usage at lower dosages from about 0.1 to 0.2 mg per kg of body weight.

The following examples will serve to further typify the nature of the invention, but should not be construed as a limitation on the scope thereof, which is defined solely by the appended claims.

EXAMPLE 1

Preparation of Three-Component Composition Comprising Pluronic L61, Doxorubicin, and PEO Doxorubicin (Sigma, St. Louis) was dissolved at different concentrations in sterilized water (Prep. A). Polyethylene oxide (PEG 8000, Sigma, St. Louis) was then dissolved in PBS at a concentration of 10% w/v, and Pluronic L61 (BASF) (0.2% w/v) was added. The mixture obtained was stirred at 4° C. until optically transparent (about 45 minutes), (Prep. B). Prep. B was then sterilized by filtration through a 0.2 μM filter. Prep. A and Prep. B were then mixed together in equal proportions (Prep. C) and incubated at 37° C. for 30 minutes.

EXAMPLE 2

In Vitro Evaluation of Anticancer Activity on Lewis Lung Carcinoma (3LL) Cell Line A highly metastatic clonal Lewis Lung Carcinoma cell subline H-59 (3LL) was used to evaluate cytotoxic activity of Prep. C and compare it with that of doxorubicin. To this end, the cells were suspended in RPMI 1640 medium supplemented with 10% fetal calf serum, and plated at 2000–3000 cells/well into 96-well microtiter plates. Prep. C in which doxorubicin final concentrations varied from 1 to 10,000 ng/ml was added to the cells and incubated for 2 hours at 37° C. and 5% $CO_2$. The cells were then washed three times with RPMI 1640 and cultured for 4 days. Drug cytotoxicity was determined by a standard XTT assay. To this end, sterile 1 mg/ml XTT solution in RPMI 1640 containing 5 μl/ml of 1.54 μg/ml phenazine methasulfate solution in sterile PBS was added to the cells (100 μl/well) and incubated for 4 to 16 hours at 37° C. and 5% $CO_2$. The absorbance at $\lambda_{420}$ was determined using a microplate reader. All the experiments were carried out in triplicate. SEM values were less than 10% (P<0.05). the concentrations of free doxorubicin and doxorubicin in Prep. C producing 50% inhibition of cell growth ($IC_{50}$) are presented in Table 1.

TABLE 1

| Preparation | $IC_{50}$, ng/ml doxorubicin |
|---|---|
| Prep. C | 40 |
| Doxorubicin | 110 |

EXAMPLE 3

Effect of Three Component Composition on Metastasis Development

A highly metastatic clonal subline H59 of Lewis Lung, Carcinoma (3LL-H59) was used as a model. This cell line was established using the s.c. grafting of a rare spontaneous lung metastasis detected in a mouse bearing a 3LLc s.c. tumor in the axillary region. Previous studies showed that this cell line exhibits a good pattern of organ-selective metastasis. These cells were cultured in D-MEM supplemented with 10% FCS at 37° C. in a humidified atmosphere with 5% $CO_2$. After 7 to 10 passes in culture, the cells in their logarithmic growth phase were harvested with trypsin for the following experiments.

Animals. Female C57BL/6 mice were obtained from Charles River Canada Inc. (St. Constant, Quebec, Canada) and used at 6 to 7 weeks of age. Animals were grouped five per cage with air filter cover under a light (12-h light/dark cycle, light on at 06h00) and temperature-controlled environment (22 ±1° C.). All manipulations of animals were performed under a sterilized laminar. The animals had ad libitum access to Purina Mouse Chow (Pro Lab PMH 4018, Trademark of Agway, Syracuse, N.Y.) and water. Animal studies were conducted according to the "Guidelines for Care and Use of Experimental Animals."

The animals were injected i.v. with the cells ($5 \times 10^5$ cells/animal) and were randomly divided into the four groups (10 animals per group). The animals received the following treatments: 1) Control (isotonic solution), 2) Dox (5.0 mg/kg), 3) Dox/L61 [(5.0 mg/kg)/(0.25% w/v)], 4) Dox/L61/PEG8000 [(5.0 mg/kg)/(0.25% w/v)/(1% w/v)]. Injection volumes were 100 $\mu$l per animal for all experimental groups. The treatments were performed 3 times at Day 1, Day 4 and Day 7 after tumor inoculation.

At Day 16 after tumor inoculation, the animals were sacrificed and subjected to routine metastasis inspection. All organs were routinely screened, although metastatic formations were normally detected only in the lung. Metastatic colonies on the organ surface were enumerated immediately following removal of the organs. Where the number of metastatic nodules on the organ surface was equal to or greater than 50, the animal was considered to have 50 metastasis sites. The results are presented in Table 2. The data are expressed as means±SEM for the number of metastatic sites and as the percentage of the animals having metastasis for the incidence of metastasis development. Statistical significance was calculated according to the multiple range test of Duncan-Kramer. Analysis of the incidence of metastasis development was done using the Fisher's exact test.

TABLE 2

| Group | Number of metast. sites on lung periphery ±SEM | Incidence, % |
|---|---|---|
| Control | >50 | 100 |
| Dox | 8.90 ± 2.56 | 100 |
| Dox/L61 | 0.67 ± 0.55 | 20 |
| Dox/L61/PEG | 0 | 0 |

EXAMPLE 4

Effect of Compositions on WBC Count

Cells. The same as in Example 3.

Animals. The same as in Example 3.

The animals were injected i.v. with the cells ($5 \times 10^5$ cells) and randomly divided into four groups (10 animals per group). The animals received the following treatments: 1) Control (isotonic solution), 2) Dox (5.0 mg/kg), 3) Dox/L61 [(5.0 mg/kg)/0.25% w/v)], 4) Dox/L61/PEG8000 [(5.0 mg/kg)/(0.25% w/v)/(1% w/v)]. The injection volumes were 100 $\mu$l per animal, for all experimental groups. The treatments were performed 3 times at Day 1, Day 4 and Day 7 after tumor inoculation.

At Day 16 after tumor inoculation, the blood samples (20 $\mu$l) were collected from the lateral tail vein. Each sample was supplemented with 400 $\mu$l of 3% acetic acid, incubated for 20 minutes, and the number of leukocytes was counted (WBC per ml blood).

The results are presented in Table 3. The data were treated by Student's criteria and expressed as means±SEM.

TABLE 3

| Group | WBC count per ml of blood ±SEM |
|---|---|
| Control | 12346 ± 834 |
| Dox | 2134 ± 321 |
| Dox/L61 | 5478 ± 235 |
| Dox/L61/PEG | 10358 ± 978 |

What is claimed:

1. In a pharmaceutical composition comprising an anti-neoplastic agent, the improvement in which said agent is incorporated into micelles of at least one poly(oxyethylene)-poly(oxypropylene) block copolymer and an effective amount of at least one of a non-toxic water-soluble homopolymer and a non-toxic water-soluble random copolymer.

2. A composition according to claim 2 wherein the poly(oxypropylene) portion of said block copolymer comprises at least 50% by weight of the block copolymer.

3. A composition according to claim 1 wherein the molecular mass range for the nontoxic water-soluble homopolymer or random copolymer is from about $0.5 \times 10^3$ to about $0.5 \times 10^5$.

4. A composition according to claim 1 wherein the non-toxic water-soluble polymer concentration is from about $1 \times 10^{-4}$ to about 25% w/v.

5. A composition according to claim 4, wherein the nontoxic water-soluble polymers are selected from the group consisting of N-(2-hydroxypropyl)-methacrylamide copolymers, poly(ortho esters), poly(vinyl pyrrolidone), poly(vinyl alcohol), polysaccharides and derivatives thereof.

6. A composition according to claim 1 wherein the water-soluble nontoxic homopolymer is poly(ethylene oxide).

7. A composition according to claim 1 wherein said anti-neoplastic agent is an anthracycline antibiotic.

8. A composition according to claim 7 wherein the anthracycline antibiotic is selected from the group consisting of doxorubicin, daunorubicin, and epirubicin.

9. A composition according to claim 1 wherein said antineoplastic agent is doxorubicin, said block copoyrner has a hydrophobe weight of about 1750 and a hydrophobe percentage of about 90%, and said homopolymer is PEO.

10. A method of treating a mammal suffering from neoplasm comprising administering to said mammal a therapeutic amount of a composition according to claim 1.

* * * * *